United States Patent [19]
Miller et al.

[11] Patent Number: 5,464,394
[45] Date of Patent: Nov. 7, 1995

[54] MULTILUMEN PERCUTANEOUS ANGIOSCOPY CATHETER

[75] Inventors: Arnold Miller, Chestnut Hill, Mass.; Daniel R. Lucas, Orange, Calif.

[73] Assignee: American BioMed, Inc., The Woodlands, Tex.

[21] Appl. No.: 73,781

[22] Filed: Jun. 8, 1993

[51] Int. Cl.$^6$ ................................................. A61M 29/00
[52] U.S. Cl. ........................... 604/96; 604/282; 606/194
[58] Field of Search .......................... 604/96, 101, 280, 604/282, 95; 606/192, 194; 128/656–658

[56] References Cited

U.S. PATENT DOCUMENTS

| | | | |
|---|---|---|---|
| 3,612,058 | 10/1971 | Ackerman | 604/170 X |
| 4,579,127 | 4/1986 | Haacke | 128/772 |
| 4,718,423 | 1/1988 | Willis et al. | |
| 4,737,142 | 4/1988 | Heckele | 604/95 |
| 4,770,653 | 9/1988 | Shturman | |
| 4,795,434 | 1/1989 | Kujawski | |
| 4,800,886 | 1/1989 | Nestor | |
| 4,800,890 | 1/1989 | Cramer | |
| 4,808,164 | 2/1989 | Hess | |
| 4,830,460 | 5/1989 | Goldenberg | |
| 4,838,269 | 6/1989 | Robinson et al. | |
| 5,090,959 | 2/1992 | Samson et al. | 604/96 |
| 5,263,928 | 11/1993 | Trauthen et al. | 604/53 |
| 5,279,562 | 1/1994 | Sirhan et al. | 604/96 |

OTHER PUBLICATIONS

Product brochure of Baxter Healthcare Corporation.
Article entitled Routine Intraoperative Angioscopy in Lower Extremity Revascularization, vol. 124, May 1989.

Primary Examiner—Corrine M. Maglione
Attorney, Agent, or Firm—Gunn & Associates

[57] ABSTRACT

An improved percutaneous angioscopy catheter having a multipurpose lumen to allow simultaneous irrigation and passage of an angioscope. The angioscopy catheter includes an elongated flexible tube having a distal end adapted for insertion through a blood vessel of a patient and a proximal end adapted for connection to apparatus disposed outside the body of the patient. The elongated flexible tube also has a central lumen extending axially through the tube which is adapted to irrigate the blood at the distal end of the angioscope and changeably mount an angioscope through the central lumen. In one embodiment, the elongated flexible tube further includes at least one balloon lumen extending axially through the tube and an inflatable occlusion balloon near the distal end of the tube, and at least one stranded stainless steel wire extending axially through the tube in order to provide a predetermined rigidity to the tube. A coil spring may also be provided along the wall of the central lumen for facilitating the insertion of an angioscope through the central lumen.

19 Claims, 1 Drawing Sheet

MULTILUMEN PERCUTANEOUS ANGIOSCOPY CATHETER

BACKGROUND OF THE DISCLOSURE

The present invention relates to percutaneous angioscopy catheters, and more particularly to percutaneous angioscopy catheters which have multiple lumens.

Angioscopy is increasingly being used to observe the interior of blood vessels during a variety of procedures including, for example, lower extremity revascularization. The use of an angioscope allows the surgeon to immediately detect and correct technical errors and deficiencies, while the surgery is being performed. Angioscopy may also facilitate intraluminal therapeutic procedures, such as thrombectomy and embolectomy. Advances in fiberoptic technology and the availability of flexible angioscopes as small as a millimeter or less, allow access to most blood vessels of the body. However, despite these advances, the inability to see through blood because of the opaque nature of the blood and the resulting need for removal of blood from the visual field remain the primary obstacles to the widespread and routine use of angioscopy during lower extremity revascularization and other procedures.

In percutaneous angioscopy, the angioscope is inserted through the skin and into a blood vessel by means of a catheter which has a bore or "lumen" through which the angioscope is passed. An angioscopy catheter typically requires additional channels or lumens through which a variety of procedures are performed, such as balloon inflation and deflation, irrigation, etc. More specifically, in percutaneous angioscopy, a fluid is typically delivered through a separate lumen to a balloon provided at the distal end of the lumen to inflate the balloon and thereby occlude the blood vessel and prevent the flow of blood. Often through yet another lumen. the blood vessel at the distal end of the catheter is irrigated with a liquid such as a saline solution to clear the viewing area adjacent the angioscope. Such multiple lumens often cause the catheter to have an undesirably large diameter. It is well known that the insertion of a large angioscopy catheter into a blood vessel can cause an irreversible spasm in the blood vessel or other serious damage to the interior wall of the vessel. Therefore, the diameter of an angioscope catheter should be kept as small as practical. On the other hand, if multiple lumens are provided within a catheter having a relatively small diameter, the efficiency of the lumens, particularly the irrigation and balloon inflation/deflation lumens, can be significantly impaired.

Further, a percutaneous catheter requires "pushability" to prevent a catheter from collapsing as the catheter is being inserted, as well as flexibility to maneuver through blood vessels which curve, convolute and angle. If the diameter of a catheter is made small, the percutaneous catheter may not have a sufficient rigidity to provide the desired pushability. On the other hand, increasing the diameter of the catheter to increase rigidity is limited by other considerations, including minimizing damage to the blood vessel as noted above.

SUMMARY OF THE INVENTION

It is, therefore, an object of the present invention to provide an improved percutaneous angioscopy catheter obviating, for practical purposes, the above-mentioned limitations.

It is another object of the present invention to reduce the size of a percutaneous angioscopy catheter by providing multi-purpose lumens therewith to be adapted for free passage and withdrawal of an angioscope, as well as for irrigation to clear the blood from the distal end of the angioscope, while maintaining sufficient rigidity.

These and other objects and advantages are achieved in a percutaneous angioscopy catheter which, in the illustrated embodiment, includes an elongated flexible member or tube having a distal end adapted for insertion through a blood vessel of a patient and proximal end adapted for connection to apparatus disposed outside the body of the patient. The elongated flexible tube further has a central lumen extending axially through the tube which is adapted to receive an angioscope and simultaneously to irrigate the blood at the distal end of the angioscope. The central lumen may also provide a passage for a guide wire.

In a preferred embodiment, the elongated flexible tube includes two stranded stainless steel wires spaced from each other and extending axially through the tube in order to provide a predetermined rigidity to the tube. The stranded wires provide "pushability" or appropriate rigidity to minimize collapsing the catheter as it is inserted into the blood vessel.

Further, a coil spring may be provided along the wall of the central lumen to facilitate the insertion of an angioscope through the central lumen. The elongated flexible tube of the illustrated embodiment also has at least one balloon lumen extending axially through the tube and an inflatable occlusion balloon near the distal end of the tube.

As a result, a percutaneous angioscopy catheter of the present invention may have a small external diameter and yet sufficient axial rigidity and lateral flexibility to enable the catheter to push through blood vessels without collapsing. In addition, despite the small external diameter, the catheter of the present invention has a relatively large central lumen which enables simultaneous angioscopy and sufficient irrigation through the same lumen.

Because of these and other features, the angioscopy catheter system of the present invention is suitable for percutaneous angioscopy of peripheral blood vessels and grafts and abdominal and major branches.

So that the manner in which the above recited features, advantages and objects of the present invention are attained and can be understood in detail, a more particular description of the invention, briefly summarized above, may be had by reference to the embodiments thereof which are illustrated in the appended drawings.

It is to be noted, however, that the appended drawings illustrate only typical embodiments of this invention and are therefore not to be considered limiting of its scope, for the invention may admit to other equally effective embodiments.

DESCRIPTION OF THE PREFERRED EMBODIMENT

Figure 1:
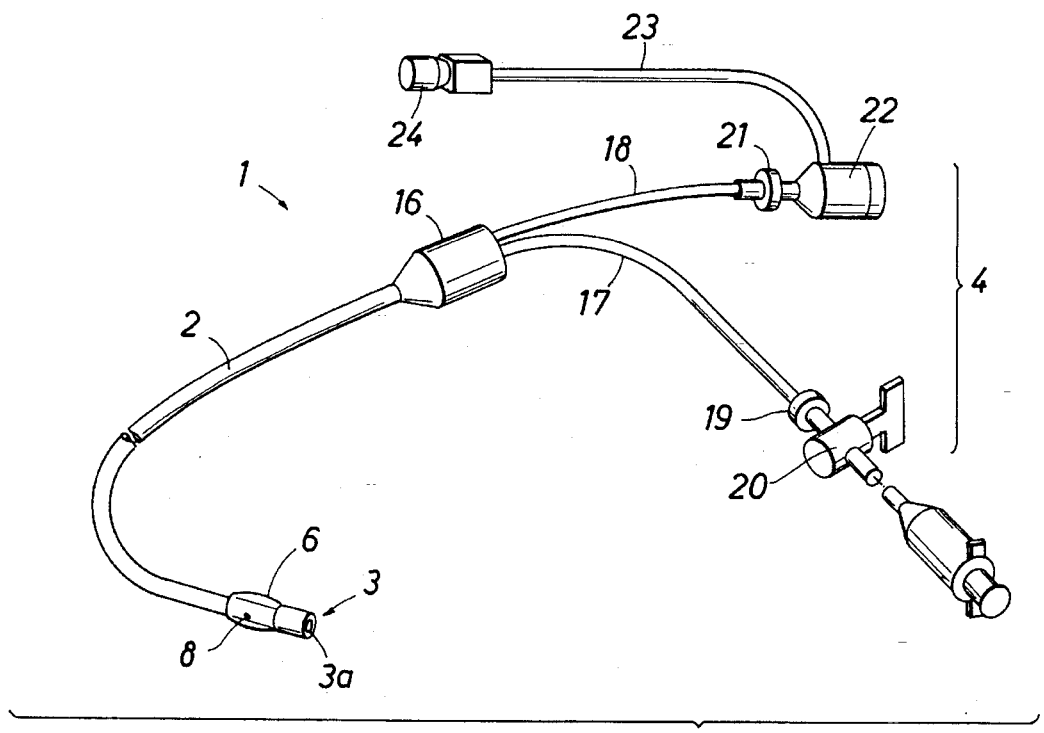
FIG. 1 is a perspective view of a percutaneous angioscopy catheter system in accordance with a preferred embodiment of the present invention.

A percutaneous angioscopy catheter system in accordance with a preferred embodiment of the present invention is illustrated in FIG. 1 and is generally indicated at 1. The percutaneous angioscopy catheter system I includes an elongated flexible member or tube 2 having a distal end 3 adapted for insertion through a blood vessel of a patient and a proximal end 4 adapted for connection to angioscopy apparatus disposed outside the body of the patient. The proximal end 4 is adapted for connection to angioscopy apparatus disposed outside the body of the patient such as a video camera as an example (not shown) for continuous monitoring of the interior of blood vessels. The flexible tube 2 has an outside diameter of from 6 French to 8 French (The "French" is a customary unit of measure for catheter and needle diameters; one French being equal to a third of a millimeter). According to one embodiment, the flexible tube has an outside diameter of 0.105 inches (approx. 2.6 mm). The flexible tube 2 is generally made of a extruded flexible material such as polyester polyethylene, and silicone rubber as examples. According to one embodiment, the flexible tube 2 is formed with Dow-Corning medical grade silicone rubber 80 SHORE DOW Q7-4780. The flexible tube 2 may be provided with markers on its outer surface at suitable intervals (for example, 100 mm) for determining how much of the catheter has been inserted into a patient's body.

Figures 2, 3:
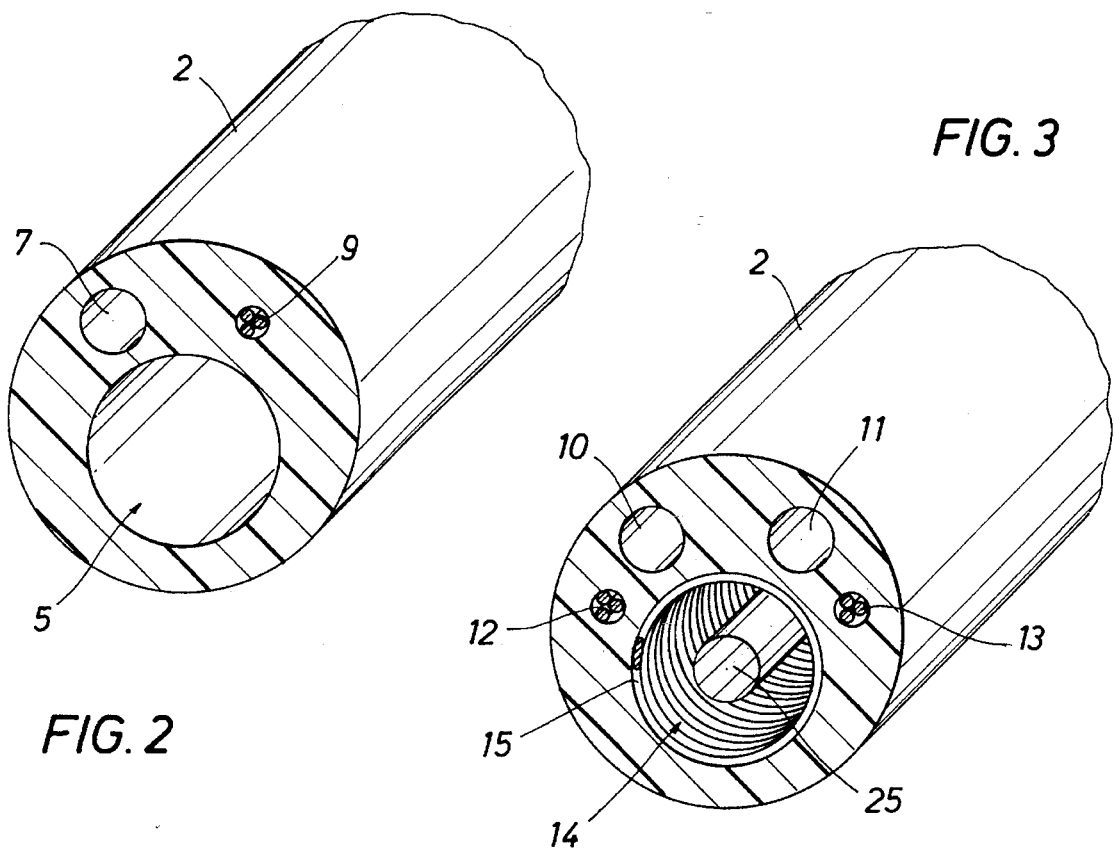
FIG. 2 is a cross-section of the catheter of FIG. 1.
FIG. 3 is a cross-section of an alternative embodiment of the catheter of FIG. 2.

Referring now to FIG. 2, the elongated flexible tube 1 includes a central lumen 5 extending axially through the flexible tube 2 and communicating with an open port 3a at the distal end 3 of the tube 2. The central lumen 5 may provide a passage for a guide wire to guide the catheter through blood vessels. When the distal end of the catheter is placed at a point of interest in a blood vessel, the guide wire is exchanged for an angioscope. The central lumen 5 is adapted to receive an angioscope and simultaneously to irrigate the blood at the distal end of the angioscope. The central lumen 5 has a sufficient interior diameter to provide ample spacing between the exterior of the angioscope and the interior wall of the central lumen 5 to allow sufficient irrigation for clearing the blood at the distal end of the catheter with an angioscope of 0.8 mm or smaller diameter mounted within the central lumen 5. By way of example, the central lumen 5 has a luminal diameter of 0.065 inches (approx. 1.65 mm) in order to achieve an irrigation liquid flow rate of up to 200 ml/min. with an angioscope of 0.8 mm diameter placed within the central lumen 5.

The elongated flexible tube 2 also has a balloon lumen 7 having a luminal diameter of 0.02 inches (0.5 mm), and extending axially through the flexible tube 2 and substantially in parallel with the central lumen 5. An inflatable member such as a balloon 6 is affixed near the distal end of the flexible tube 2 as shown in FIG. 1. An inflating fluid is delivered through the balloon lumen 7 to the balloon 6 to inflate the balloon and thereby occlude the blood vessel and prevent the flow of blood. The balloon 6 substantially covers the external surface of the flexible tube 2 near the distal end 3 thereof, and is affixed over a port 8 which is provided in the wall of the flexible tube 2 and communicates with the balloon lumen 7. The balloon 6 may be made of a suitable inflatable material such as a medical grade silicone rubber. Latex, polyethylene and other inflatable materials may also be used for the balloon 6. However, it has been discovered that a balloon made of silicone rubber has increased reliability and safety in angioscopy because a balloon made of silicone rubber does not tend to fragment if it punctures, thereby avoiding polluting the blood of the patient with fragmented balloon material.

According to one embodiment of the present invention, to form the balloon 6, a separation compound which prevents adhesion of melted silicone rubber is applied to a strip of approximately 10 mm width around the tube 2 over the port 8.

The flexible tube 2 is generally formed by a flexible soft material, as previously mentioned, such as silicone rubber and the diameter of the central lumen 5 is large with regard to the outside diameter of the flexible tube 2 in order to allow simultaneous irrigation and passage of an angioscope. As a result, the flexible tube 2 has a rather thin wall with regard to the overall size of the flexible tube 2. To provide sufficient pushability to the flexible tube 2, a supporting wire 9 is provided generally in parallel with the central lumen 5 and the balloon lumen 7. The supporting wire 9 has a diameter of about 0.015 inches (0.36 mm). and such wire is syptically radio-opaque, made of three on one stranded wires of stainless steel, or other suitable materials to provide increased axial rigidity to the flexible tube 2. Such wire is typically radio-opaque. Consequently, if the catheter is required to be pushed through a small blood vessel or tight lesions in a blood vessel, the supporting wire 9 has sufficient column strength or axial stiffness to enable the tube to advance through the blood vessel.

Referring now to FIG. 3, an alternative embodiment is shown in which an elongated flexible tube 2 having an outside diameter of 0.105 inches (approx. 2.6 mm) includes a central lumen 14 having a luminal diameter of about 0.069 inches. Two separate balloon lumens 10 and 11 each having a luminal diameter of about 0.016 inches are provided substantially in parallel with the central lumen 14. The elongated flexible tube 2 also has two supporting wires 12 and 13 each having a diameter of 0.007 inches spaced from each other and both extending substantially in parallel with the central lumen 14. The supporting wires 12 and 13, like the corresponding supporting wire 9 of FIG. 3, are formed of three on one stainless steel strands. The two balloon lumens 10 and 11 are coupled to the inflatable balloon 6 to allow rapid deflation of the balloon 6 when desired. The balloon 6 may be either pneumatically or hydraulically inflated, and the two balloon lumens 10 and 11 are particularly effective when the hydraulic inflation and deflation of the balloon 6 is utilized.

A stainless steel coil spring 15 lines the interior wall of the central lumen 14 to facilitate the insertion of an angioscope through the central lumen 14. Also the spring 15 further increases the axial rigidity of the tube 2.

As shown in FIG. 1 and FIG. 2, the percutaneous angioscopy catheter 1 of the present invention further comprises a connector 16 having a balloon lumen port 17 communicating with the balloon lumen 7 (or 10 and 11) and a central lumen port 18 communicating with the central lumen 5 (or 14). A tapered female lure fitting 19 is affixed to the proximal end of the balloon lumen port 17. In the illustrated embodiment the female lure fitting 19 of the balloon lumen port 17 is coupled to a stop cock 20 having a male lure fitting. A balloon inflation/deflation apparatus such as a syringe is coupled to the stop cock 20.

Another female lure fitting 21 if affixed to the proximal end of the central lumen port 18. A hemostatasis valve 22, for example a CORDIS® hemostatasis valve, having a male type lure fitting is coupled to the central lumen port 18 by mating with the female lure fitting 21. The hemostatasis valve 22 prevents leakage around the angioscope when the catheter is inserted in the bloodstream through the central lumen 5. An angioscope (now shown) is inserted into the central lumen 5 through the hemostatasis valve 22. The hemostatasis valve 22 includes still another port 23 which communicates with the central lumen 5 when the hemostatasis valve 22 is coupled to the central lumen port 18. A pump (not shown) or other irrigation device is connected to a connector 24 at the port 23 for pumping an irrigation liquid such as a saline solution to clean blood from the distal end of the angioscope.

In a similar fashion, the flexible tube 2 shown in FIG. 3 may be coupled to the central lumen port 18 and balloon lumen port 17.

While the foregoing is directed to the preferred embodiment of the present invention, other and further embodiments of the invention may be devised without departing from the basic scope thereof, and the scope thereof is determined by the claims which follow.

What is claimed is:

1. A percutaneous angioscopy catheter comprising:
   (a) an elongated flexible member having a distal end adapted for insertion through a blood vessel of a patient and a proximal end adapted for connection to apparatus disposed outside the body of the patient;
   (b) said elongated flexible member defining a first lumen extending axially through said elongated flexible member for slidably mounting an angioscope therein, and at least one second lumen extending axially through said elongated flexible member substantially in parallel with said first lumen;
   (c) an inflatable balloon provided on said elongated flexible member in proximity to said distal end and communicating with said second lumen;
   (d) supporting means extending axially through said elongated flexible member spaced from and substantially in parallel with said first and second lumen for providing a predetermined rigidity to said elongated flexible member; and
   (e) a coil spring provided along the interior of said first lumen for facilitating the passage of the angioscope.

2. The percutaneous angioscopy catheter of claim 1 wherein the first lumen is sized sufficiently to allow a flow of irrigation fluid between the exterior of the angioscope and the interior of the first lumen.

3. The percutaneous angioscopy catheter of claim 2 further comprising an irrigation port coupled to said first lumen for supplying an irrigation fluid for clearing the distal end of the catheter and an angioscope port coupled to said first lumen for slidably mounting an angioscope therethrough.

4. The percutaneous angioscopy catheter of claim 1 wherein said elongated flexible member is made of silicone rubber.

5. The percutaneous angioscopy catheter of claim 1 wherein said inflatable balloon is made of silicone rubber.

6. The percutaneous angioscopy catheter of claim 1 further comprising a third lumen spaced from the second lumen and coupled to the balloon to provide at least two lumens for inflating or deflating said balloon.

7. The percutaneous angioscopy catheter of claim 1 wherein said supporting means comprises a radio-opaque wire.

8. The percutaneous angioscopy catheter of claim 7 wherein said wire comprises a three on one stranded stainless steel wire.

9. The percutaneous angioscopy catheter of claim 7 further comprising a second radio-opaque wire spaced from the first wire.

10. The percutaneous angioscopy catheter of claim 9 wherein both of said wires are three on one stranded stainless steel wires.

11. The percutaneous angioscopy catheter of claim 1 further comprising a connector having a balloon lumen port communicating with the second lumen, through which a balloon inflating fluid may be injected into said second lumen and the balloon, and a central lumen port communicating with said first lumen, through which an angioscope may be passed to said first lumen, said catheter further comprising a hemostatasis valve coupled to the central lumen port for preventing leakage around the angioscope when the catheter is inserted in the bloodstream, and a stop cock coupled to the balloon lumen port for retaining the inflating fluid after it has been injected into the balloon.

12. The percutaneous angioscopy catheter of claim 11 further comprising an irrigation port coupled to said central lumen port for supplying an irrigation fluid to clear the distal end of the catheter and an angioscope port coupled to said central lumen port for slidably mounting an angioscope therethrough.

13. A percutaneous angioscopy catheter system comprising:
   (a) an elongated flexible member having a distal end adapted for insertion through a blood vessel of a patient and a proximal end adapted for instrumental connection;
   (b) a first lumen extending axially through said elongated flexible member for slidably mounting an angioscope therein;
   (c) a second lumen extending axially through said elongated flexible member substantially in parallel with said first lumen;
   (d) an inflatable balloon provided in proximity to said distal end over a port communicating with said second lumen;
   (e) supporting means extending axially through said elongated flexible member spaced from and substantially in parallel with said first and second lumen for providing a predetermined rigidity to said elongated flexible member;
   (f) a connector having a balloon lumen port communicating with said second lumen, through which a balloon inflating fluid may be injected into said second lumen and the balloon, and a central lumen port communicating with said first lumen, through which an angioscope may be passed to said first lumen;
   (g) a hemostatasis valve coupled to the central lumen port for preventing leakage around the angioscope when the catheter is inserted in the bloodstream;
   (h) a stop cock coupled to the balloon lumen port for retaining the inflating fluid after it has been injected into the balloon;
   (i) an irrigation port coupled to said central lumen port for supplying an irrigation fluid to clear the distal end of the catheter; and
   (j) a coil spring provided along the interior of said first lumen for facilitating the passage of the angioscope.

14. The percutaneous angioscopy catheter system of claim 13 wherein said elongated flexible member is made of silicone rubber.

15. The percutaneous angioscopy catheter system of claim 13 wherein said inflatable balloon is made of silicone rubber.

16. The percutaneous angioscopy catheter system of claim 13 further comprising a third lumen spaced from said second lumen and coupled to said balloon to provide at least two lumens for inflating or deflating said balloon.

17. The percutaneous angioscopy catheter system of claim 13 wherein said supporting means comprises two stranded wires spaced from each other.

18. The percutaneous angioscopy catheter system of claim 17 wherein said stranded wires each comprise a three on one stranded stainless steel wire.

19. A percutaneous angioscopy catheter comprising:
(a) an elongated flexible silicone rubber member having a distal end adapted for insertion through a blood vessel of a patient and a proximal end adapted for connection to apparatus disposed outside the body of the patient;
(b) a central lumen defined by said elongated member and extending axially though said member and adapted for irrigation of blood and changeably mounting therethrough an angioscope;
(c) a coil spring provided along the interior of said central lumen for facilitating the passage of an angioscope;
(d) an inflatable silicone rubber balloon provided in proximity to said distal end;
(e) two balloon lumens extending axially through said elongated flexible member substantially in parallel with each other and coupled to said balloon for directing a fluid to and from said balloon for inflating and deflating respectively the balloon; and
(f) two standed wires spaced from each other, each comprising a three on one stranded stainless steel wire extending axially through said member for providing a predetermined rigidity to said elongated flexible member.

* * * * *